(12) United States Patent
Guala

(10) Patent No.: US 8,133,209 B2
(45) Date of Patent: Mar. 13, 2012

(54) VALVE CONNECTOR FOR MEDICAL LINES

(75) Inventor: Gianni Guala, Turin (IT)

(73) Assignee: Industrie Borla S.p.A., Moncalieri (Torino) (IT)

( * ) Notice: Subject to any disclaimer, the term of this patent is extended or adjusted under 35 U.S.C. 154(b) by 346 days.

(21) Appl. No.: 12/463,692

(22) Filed: May 11, 2009

(65) Prior Publication Data

US 2009/0292274 A1 Nov. 26, 2009

(30) Foreign Application Priority Data

May 21, 2008 (IT) .............................. TO2008A0381

(51) Int. Cl.
*A61M 5/00* (2006.01)
(52) U.S. Cl. .................. 604/249; 604/167; 604/169
(58) Field of Classification Search .......... 604/533–284, 604/167–16, 246–256
See application file for complete search history.

(56) References Cited

U.S. PATENT DOCUMENTS 5,549,566 A * 8/1996 Elias et al. ............... 604/167.03

FOREIGN PATENT DOCUMENTS

| EP | 1 834 665 | 9/2007 |
| WO | WO 96/13301 | 5/1996 |
| WO | WO 98/26835 | 6/1998 |
| WO | WO 2006/013433 | 2/2006 |

OTHER PUBLICATIONS

European Search Report issued Sep. 10, 2010 in connection with EP App No. 09160641.8.

* cited by examiner

*Primary Examiner* — Jackie Ho
*Assistant Examiner* — Phillip Gray
(74) *Attorney, Agent, or Firm* — Nixon & Vanderhye P.C.

(57) ABSTRACT

Valve connector for infusion medical lines including an external tubular body (1) with an inlet end (4) and an outlet end (10), an internal hollow spike (2) and an intermediate sealing member (3) including an elastic head (35) with pre-slit (38) and an elastic hollow element (36) formed with sealing members (47, 48) in contact with the hollow spike (2) and with an elastic thrust means tending to maintain the elastic head (35) in a closure condition. An annular member (55) surrounds the elastic hollow element (36) and it axially slides into the tubular body (1) due to the movement of the elastic head (35) between the closure condition and the opening condition of the connector.

13 Claims, 8 Drawing Sheets

VALVE CONNECTOR FOR MEDICAL LINES

FIELD OF THE INVENTION

The present invention refers to valve connectors for medical lines, for example for infusion, by means of an introducer of a fluid infusion substance, typically a Luer connector or Luer-Lock for example of a needleless syringe.

PRIOR ART

Known from the European patent application EP-1834665A1 on behalf of the same Applicant is a valve connector according to the preamble of claim 1, wherein provided is a tubular body having a cavity, an inlet end designed for the engagement of a liquid introducer, and an outlet end. A hollow spike is arranged axially into the cavity of the tubular body and it has a closed tip facing the inlet end of the tubular body and axially spaced by the latter. The hollow spike is in communication with the outlet end of the tubular body and it has a lateral hole spaced from its closed tip for communication with the cavity of the tubular body. The connector further includes a sealing elastic member which comprises an elastic head having a pre-slit and normally arranged in a closure condition (or deactivated condition) into the inlet end of the tubular body, in which the pre-slit is closed. The elastic head is axially moveable against the closed tip of the hollow spike upon insertion of the introducer into the inlet end of the tubular body, to interact with such tip taking an elastically deformed condition of opening (or activated condition), in which the pre-slit opens. The sealing member of the valve connector further includes an elastic hollow element joined to the head, interposed between the tubular body and the hollow spike and having sealing means in contact with such hollow spike to isolate the above mentioned lateral hole with respect to the cavity of the tubular body when the head is arranged in the undeformed closure condition. The elastic hollow element includes an elastic thrust means tending to maintain the head of the sealing member in the abovementioned closure condition. Such elastic thrust means includes a base part having a generally cylindrical axial wall radially spaced from the hollow spike to define an annular chamber therewith. The base part is joined to the elastic hollow element through a generally transverse annular wall which, during the axial movement of the elastic head from the closure condition to the opening condition, bends inside the annular chamber.

This connector according to the European patent application EP-1834665A1 is easy to clean and disinfect ("swabbable") from the inlet end side, and easily meets several fundamental requirements regarding use in the medical industry.

Firstly, it is suitable to guarantee an efficient sealed closure of the inlet end of the tubular body operating from the head of the sealing member, thus ensuring a total antibacterial barrier even after multiple openings and re-closures of the valve connector.

Secondly, the opening and reclosure operation of the communication between the inlet end and the outlet end of the connector when inserting and the removal of the introducer respectively is entirely reliable and repeatable, without any risks of malfunctioning that could expose the patient connected to the valve connector to serious risks. This also derives from the fact that the number of moving mechanical members is reduced to the minimum possible.

Thirdly, this known connector is capable of satisfactorily bearing any slight overpressures that might occur therein during its use, and it guarantees an efficient resistance against positive and negative pressures in the closure or deactivated condition.

SUMMARY OF THE INVENTION

The present invention is an improvement of the valve connector known from the previously mentioned document EP-1834665A1, and in particular it has the object of increasing the airtight sealing of the connector in its activated condition, or in the elastically deformed condition of the elastic hollow element of the sealing member, even up to internal overpressures far exceeding values in the order of 100 psi.

Such object is essentially attained by virtue of a substantially inextensible annular member surrounding the elastic hollow element and axially sliding inside said tubular body upon displacement of said elastic head between said closure and opening conditions.

Furthermore the hollow spike conveniently has an external annular projection suitable to interact with the sealing means of the elastic hollow element, and in the opening condition of the elastic head the abovementioned annular member surrounding the elastic hollow element is arranged at a substantially axial position of such external annular projection.

Due to this solution idea, the valve connector according to the invention is provided with an improved degree of reliability, guaranteeing the airtight sealing in its activated condition even in case of generation of overpressures therein reaching up to values in the order of 300 psi and above in its activated condition.

BRIEF DESCRIPTION OF THE DRAWINGS

Now, the invention shall be described in detail with reference to the attached drawings, strictly provided for exemplifying and non-limiting purposes, wherein.

DETAILED DESCRIPTION OF THE INVENTION

Figure 1:
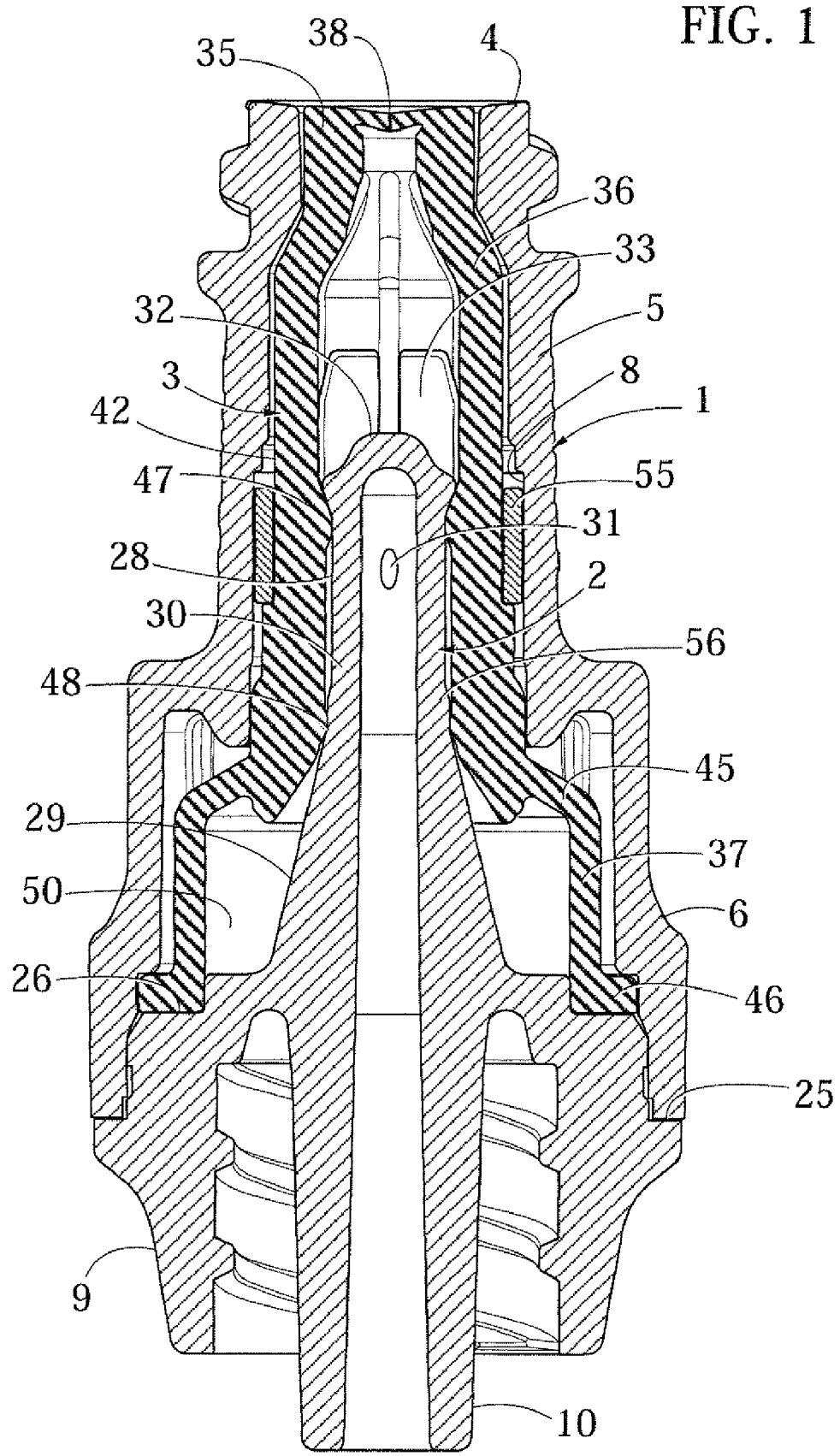
FIG. 1 is a schematic axial sectional view of the valve connector according to a first embodiment of the invention represented in deactivated condition.

In the embodiment represented in FIGS. 1-4, 8 and 9, the valve connector for infusion medical lines according to the invention is generally similar to that described and illustrated in abovementioned document EP-1834665A1 and essentially includes four components: an external tubular body 1, an internal hollow spike 2 arranged axially into the cavity of the tubular body 1, a sealing elastic member 3, and a further document described hereinafter. Typically, the tubular body 1 and the hollow spike 2 are made of moulded rigid plastic material, while the sealing member 3 is made of elastic material, for example silicone rubber.

The tubular body 1 has an inlet end 4 shaped like a female Luer-Lock connection member for the engagement, in a generally conventional manner, with a male Luer or Luer-Lock connection member of a fluid introducer, for example represented by a needleless syringe. The inlet end 4 is fitted to a generally cylindrical intermediate portion 5 followed by a widened end portion 6, also generally cylindrical.

The internal surface of the inlet end 4 has a cylindrical initial part made with axial channels 7, and the internal surface of the intermediate part 5 has, in succession towards the final portion 6, cylindrical and frusto-conical portions. An intermediate cylindrical portion is indicated with 8 and it defines a sliding guide surface described hereinafter.

The hollow spike 2 has a base generally indicated with 9, made externally with a gripping ring and shaped internally like a male Luer-Locker connection member with a central tubular shank 10 with a slightly conical external surface defining the outlet end of the valve connector 1. Such end could also be shake like a connector of any other type.

The base 9 is made with a first annular flange 25 of a larger diameter, for joining the edge of the free end of the widened end portion 6 of the tubular body 1, and an annular flange of a smaller diameter 26. Branching off integrally from such annular flange 26 is a tubular post 28 including an initial portion having a conical surface 29, divergent towards the outlet end 10 of the connector, followed by a cylindrical portion 30 made with a single lateral through hole 31. The cylindrical portion 30 has—at its free end a closed tip 32 facing the inlet end 4 of the tubular body 1 and located at a given axial distance from the latter. Projecting from the closed tip 32 is a ring of radial/axial projections 33 angularly spaced in such a manner to define radial/axial flow channels therebetween, in manner corresponding to that described and illustrated in the previously mentioned document EP-1834665A1.

In the embodiment described herein with reference to FIGS. 1-4 the closed tip 32 is fitted to the cylindrical portion 30 through a conical surface.

Figure 2:
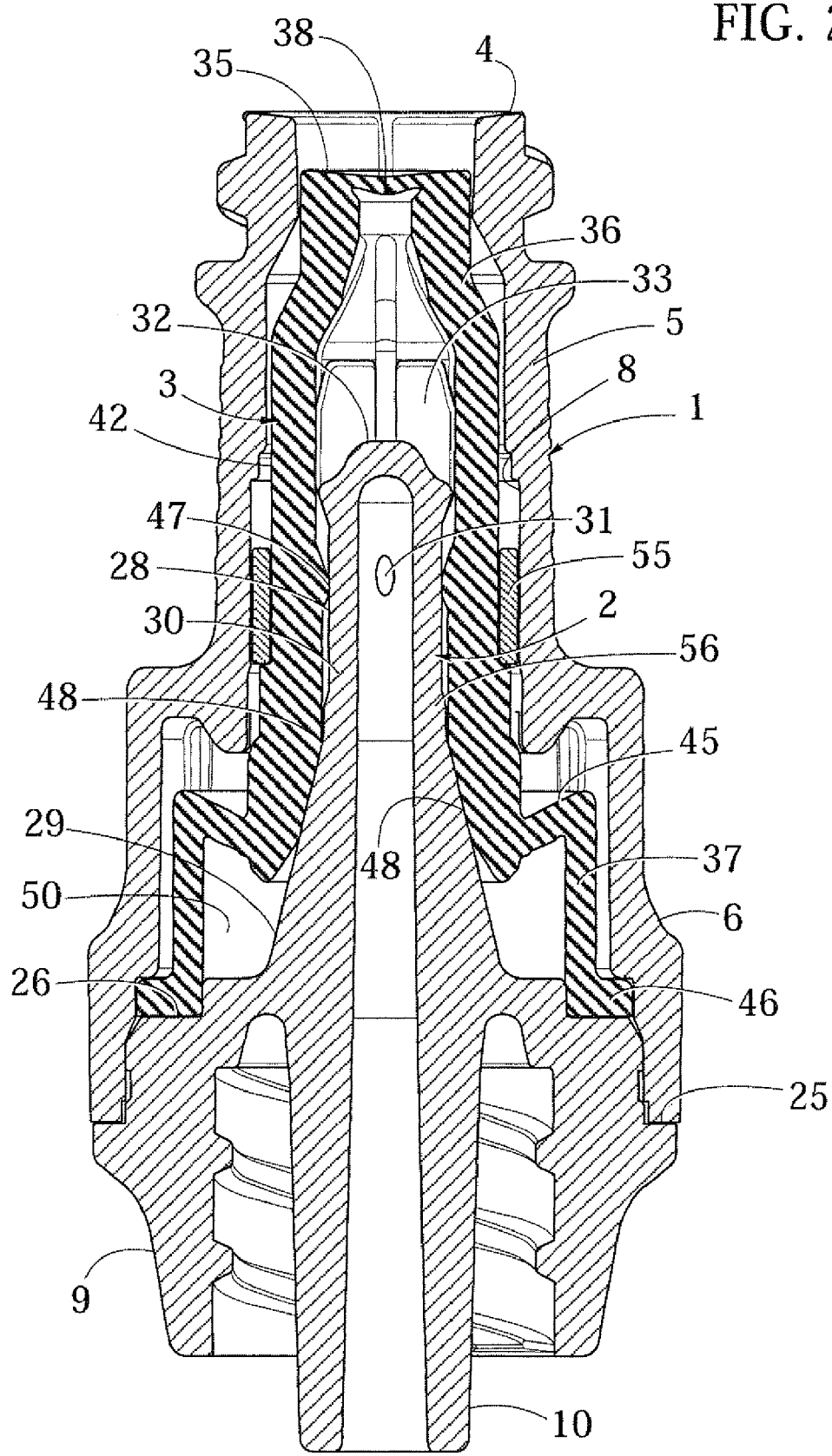
FIGS. 2, 3 and 4 are views analogous to FIG. 1 representing the valve connector in various successive operating conditions up to the condition of complete activation.
Figure 3:
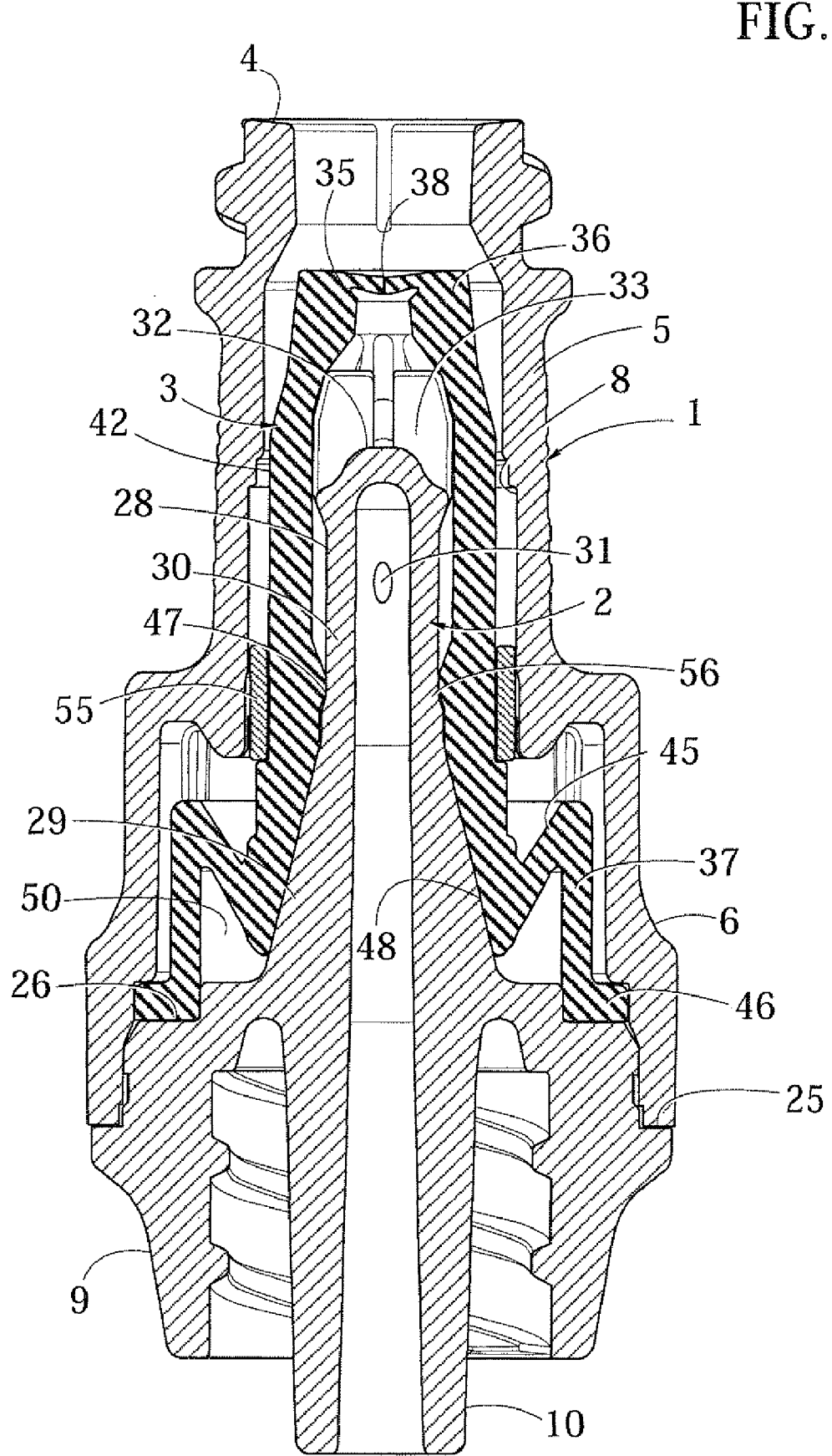
Figure 4:
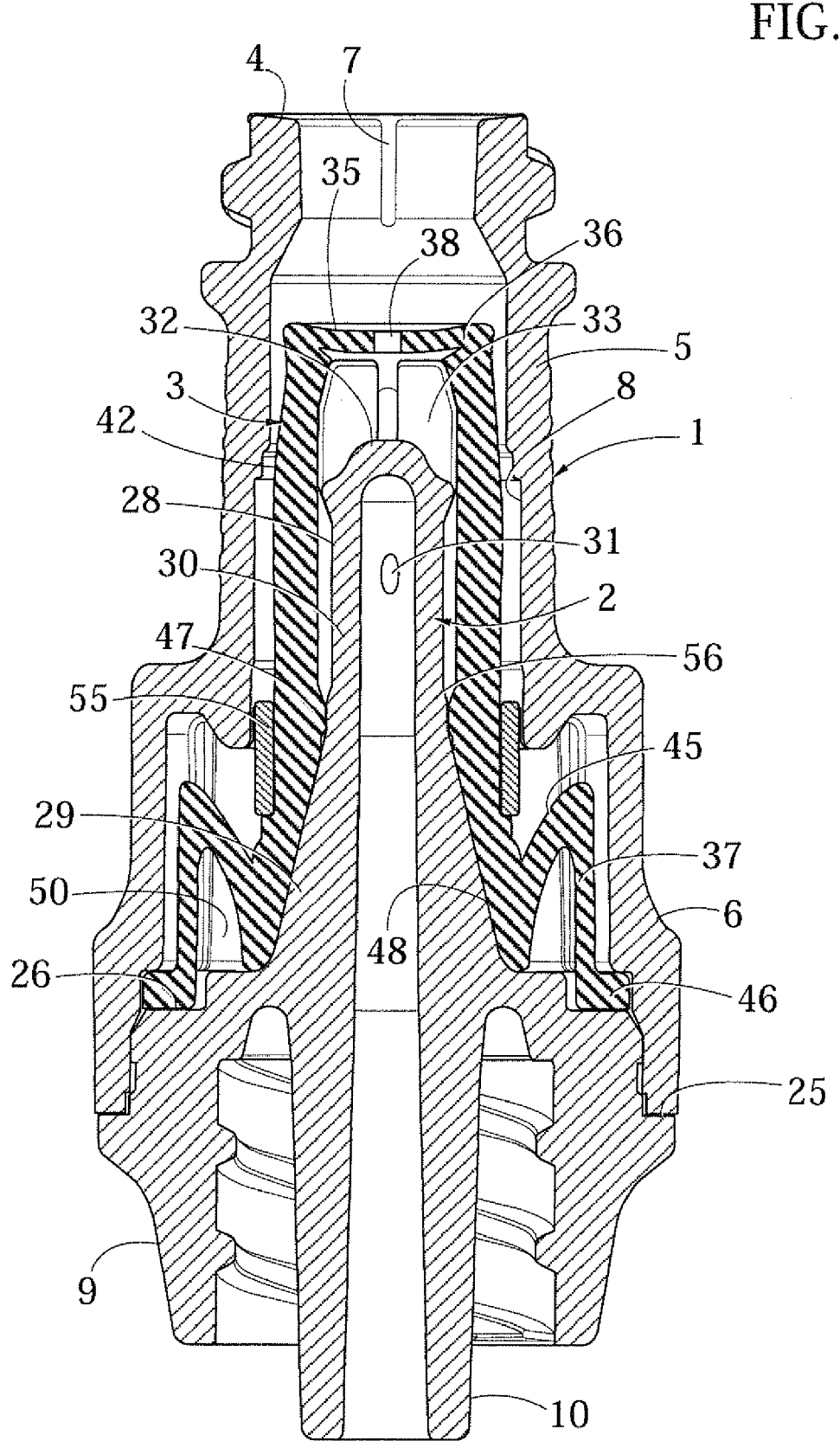

The sealing member 3 comprises, in a single piece, an elastic head 35, an elastic hollow element 36 and an elastic base 37. The general shape of the sealing member 3, and in particular its external configuration, substantially corresponds to that of the cavity of the tubular body 1, inside which it is accommodated. Thus, the elastic head 35 has a cylindrical external surface complementary to that of the internal surface of the inlet end 4 in such a manner to be accommodated therein, as represented in FIGS. 2 and 3, with slight radial clearance or without substantial interference, in a closure condition in which such head 35 is substantially undeformed and substantially flushed with respect to the inlet end 4.

Figure 9:
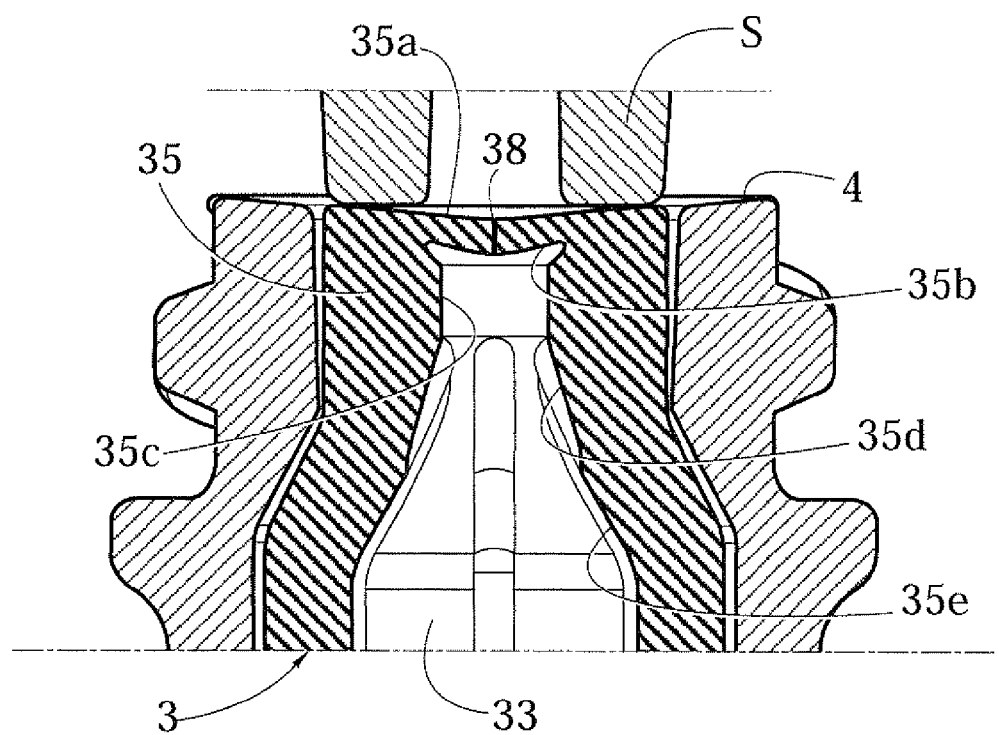
FIG. 9 shows an enlarged view of a detail of FIG. 1 or FIG. 5.

The elastic head 35 conveniently has the configuration represented more in detail in FIG. 9, with an end well 35a having an external surface slightly concave and an internal annular recess 35b shaped in the illustrated manner and connected to the internal wall of the sealing member 3 through a generally cylindrical part 35c followed by a first portion having a conical surface 35d with lower conicity and by a second portion having a conical surface 35e with greater conicity.

Formed through the wall 35a of the head 35 is a pre-slit or axial notch 38 which, in the undeformed closure condition of the elastic head 35 into the inlet end 4, is maintained gripped due to the elasticity of the head 35. In such condition, an anti-bacterial protection barrier is formed between the inside of the valve connector and the outside, ensuring at the same time the possibility of an effective cleaning conventionally performed by means of a swab soaked in a disinfectant.

The external lateral surface of the elastic hollow element 36 has a general configuration complementary, with clearance, to that of the internal surface of the tubular body 1, having cylindrical and frustoconical portions. An intermediate cylindrical portion is indicated with 42.

The elastic base 37 is fitted to the elastic hollow element 36 through a generally transverse wall 45 which, in the undeformed condition of the sealing member 3, has a frustoconical configuration.

The elastic base 37 ends, on the part opposite to the elastic head 35, with an external annular flange 46 through which such elastic base 37 is gripped and blocked axially against the annular shoulder 26 of the base 9 of the hollow spike 2.

Internally, the sealing member 3 is formed with a first annular projection 47 and with a second annular projection 48 axially spaced from each other and adapted to respectively define, through the method outlined hereinafter, a first and a second sealing member. In the closure condition of the valve connector represented in FIG. 1, the first internal sealing member 47 of the sealing member 3 is arranged in sealing contact against the surface of the tip 32 of the hollow spike 2, while the second sealing member 48 is arranged in sealing contact against the zone of the cylindrical part 30 adjacent to the conical part 29. Such zone, illustrated more in detail in FIG. 8 and indicated with 30a, has an external diameter slightly greater than that of the cylindrical part 30 and it is formed with an external annular projection 56 adapted to cooperate, in the manner outlined hereinafter, with the sealing member 47.

The lateral hole 31 of the hollow spike 2 is usually hermetically isolated by the sealing members 47 and 48 with respect to the inlet end 4 of the connector, whose communication with the outlet end 10 is thus closed.

Defined between the base 37 of the elastic sealing member 3 and the frusto-conical part 29 of the hollow spike 2 is an annular chamber 50 which communicates with the external of the valve connector through one or more passages made in the base 9 of the hollow spike 2, and whose internal pressure is thus the atmospheric pressure.

Indicated with 55 is a substantially inextensible ring, for example made of rigid plastic material, which represents the fourth component of the connector and externally surrounds the elastic hollow element 36 of the sealing member 3. The ring 55 is engaged onto the cylindrical portion 42 of the elastic hollow element 36, at a substantially axial position with respect to the sealing member 47, and it is guided with clearance in an axially sliding manner along the internal cylindrical portion 8 of the tubular body 1. The ring 55 may be provided internally, in the median zone thereof, with an annular projection not visible in the drawing, having the function of improving its gripping on the elastic hollow element 36.

As mentioned, FIG. 1 represents the watertight closure condition of the valve connector.

Given that the tip of a needleless syringe or a cone-shaped Luer introducer (schematically and partially indicated with S in FIG. 9) is rested at the front against the elastic head 35 and hence inserted into the inlet connector 4, the elastic head 35 is pushed axially towards the inside of the connector due to the elastic deformation of the sealing member 3 and, more in particular, to the deflection of the wall 45 of the elastic base 37 inside the annular chamber 50. The subsequent translation of the elastic hollow element 36 causes a corresponding movement of the ring 55 towards the frusto-conical part 29 of the hollow spike 2 (FIG. 2).

Proceeding with insertion of the introducer (FIG. 3), the wall 45 continues to undergo deflection inside the annular chamber 50, deforming progressively. The elastic head 35 and the elastic hollow element 36 of the sealing member 3 then slide progressively into the tubular body 1 and along the tubular post 28 of the hollow spike 2, in such a manner that the first sealing member 47 moves away from the conical surface 32a of the tip 32, while the second sealing member 48 slides along the conical part 29.

Simultaneously, the projections of the tip 32 of the hollow spike 2 start to interact from inside with the elastic head 35 which, due to its distinctive configuration and in particular due to the annular cavity shape 35b and the presence of the portion having a conical surface 35d, and due to the axial thrust exerted by the introducer S against the wall of a tip 35a, is subjected to a radial axial elastic deformation making the wall of the tip 35a to acquire a configuration radially dilated outwards, in such a manner to start opening the pre-slit 38.

After a complete insertion of the introducer (FIG. 4) the pre-slit 38 is entirely open, while the first sealing member 47 is arranged beneath the lateral hole 31 of the hollow spike 2. The second sealing member 48 is moved by sliding up to the widest part of the conical part 29 of the hollow spike 2, and the wall 45 is entirely deflected into the annular chamber 50. The valve connector is thus in an opening condition, with the inlet end 4 in communication with the outlet end 10 through the pre-slit 38, the lateral hole 31 and the tubular post 28.

In such condition, the sealing member 47 of the elastic hollow element 36 and the external ring 55 are substantially arranged at the external annular projection 56 of the hollow spike 2, in such a manner to guarantee a tight and safe sealed closure even in case of occurrence—inside the connector—of unusual overpressures in the order of 300 psi and above, due to which the ring 55 further translates towards the outlet end 10 further gripping the wall of the sealing member 3 against the conical part 29 of the hollow spike 2.

When the introducer S is removed from the inlet end 4, the overall elastic return of the wall 45 and of the sealing member 3 promptly restores the closure configuration of the valve connector, in which the elastic head 35 returns to the undeformed condition in the inlet end 4 reclosing the pre-slit 38, and the lateral hole 31 is once again isolated by the sealing members 47 and 48. The ring 55 thus returns to the initial position.

Figure 5:
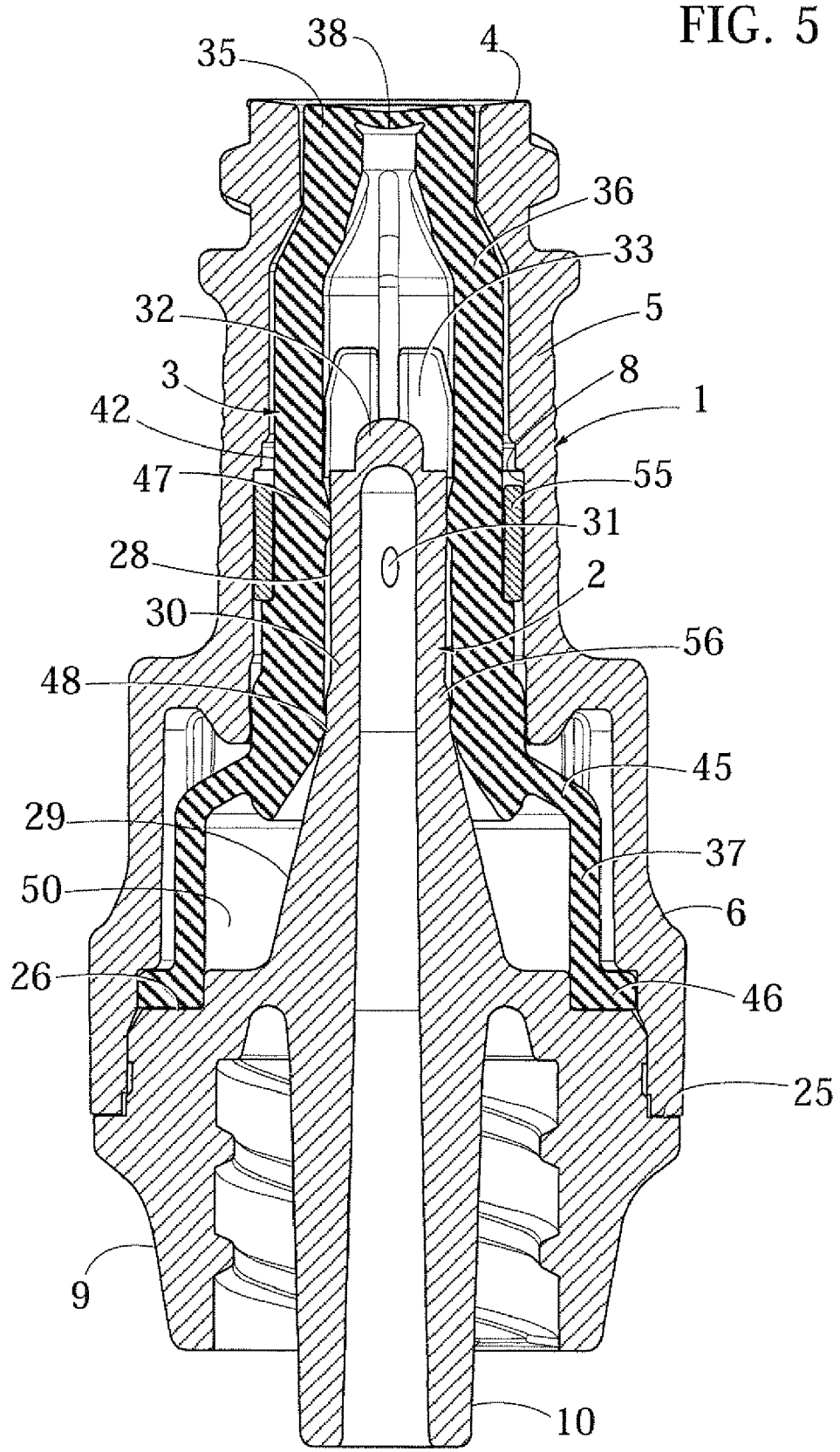
FIG. 5 is a view analogous to FIG. 1 of a variant of the valve connector according to the invention.
Figure 6:
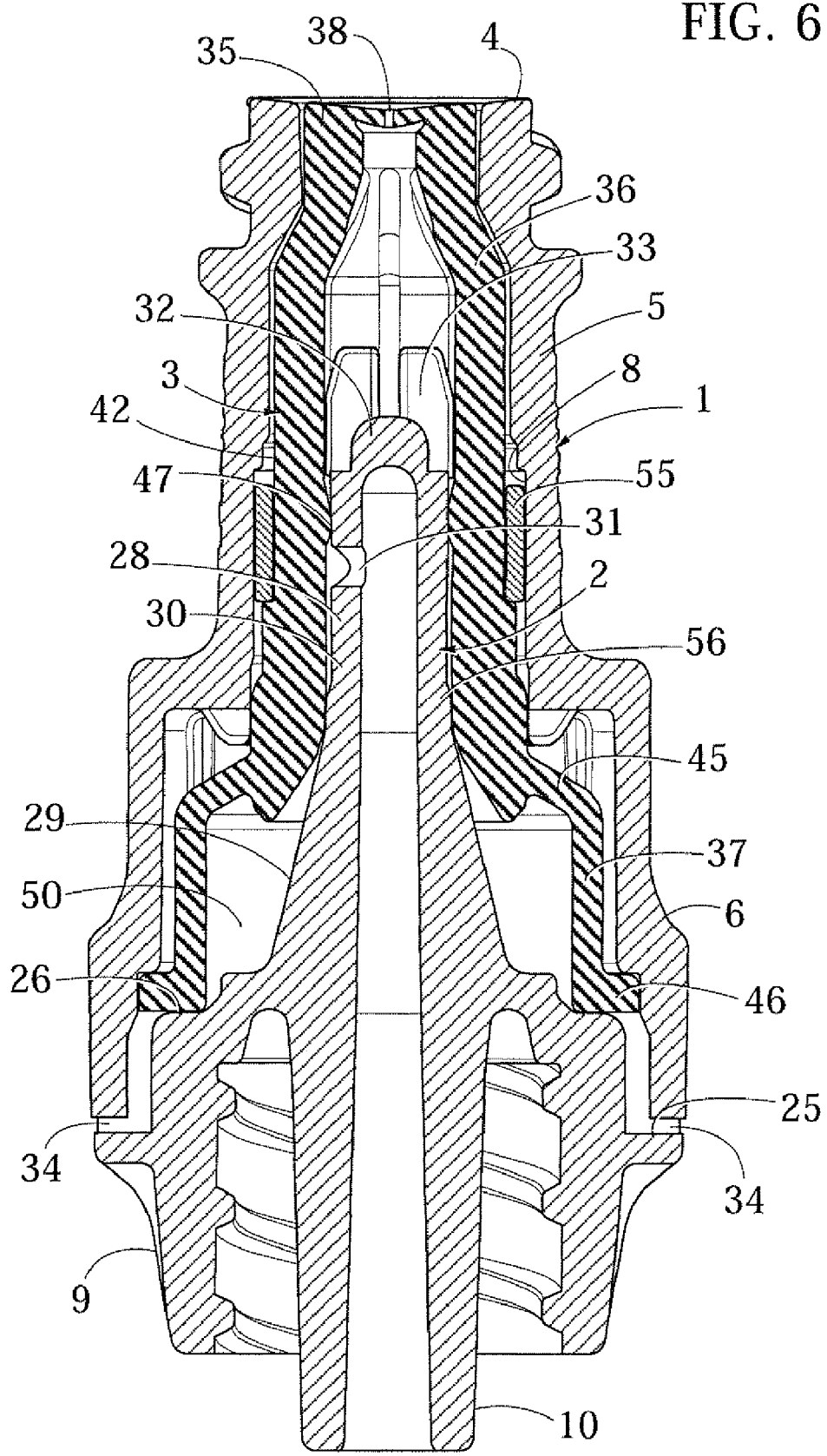
FIG. 6 is an axial sectional view of FIG. 1 rotated by 90°.
Figure 7:
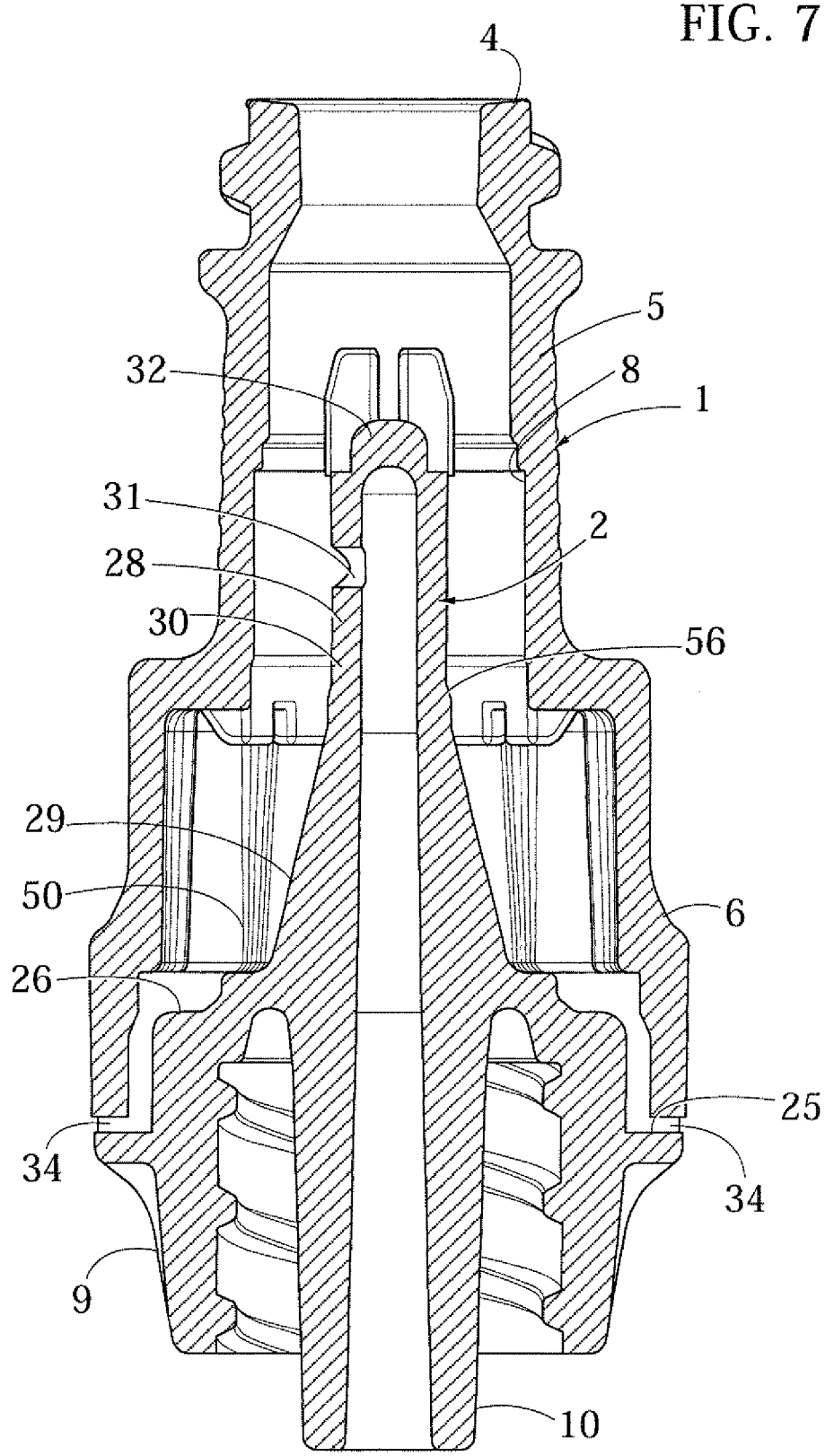
FIG. 7 is a view identical to FIG. 6 wherein a component of the connector was falsely omitted for a better observation of the configuration of another component.
Figure 8:
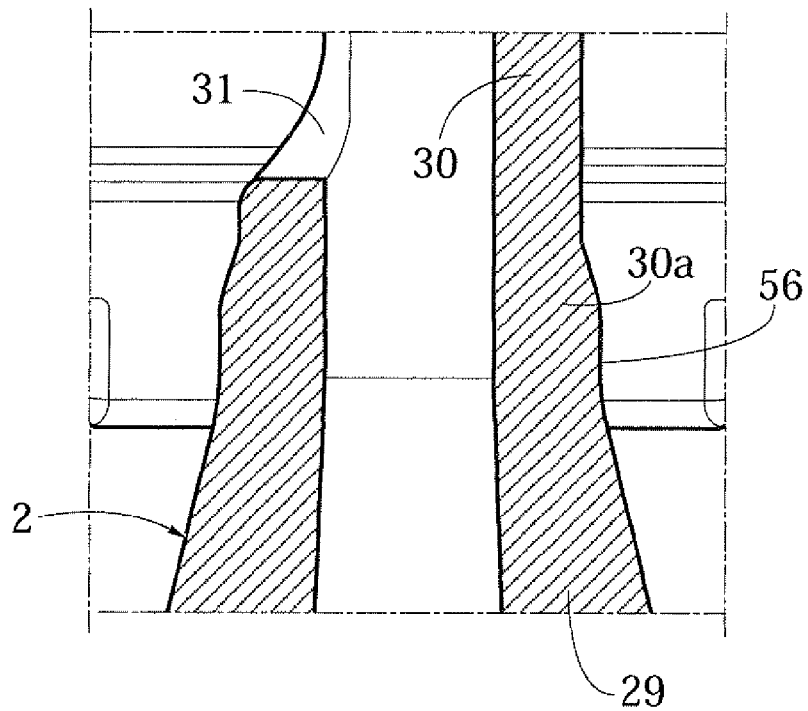
FIG. 8 shows an enlarged view of a detail of FIG. 7.

The variant illustrated in FIGS. 5-7 is generally similar to the embodiment described previously and thus only the differences shall be described in detail, using the same reference numbers for the identical or similar parts.

In such variant, the tubular post 28 of the hollow spike 2 is cylindrical internally, or it is without the portion having a conical surface for connecting with the tip head 32 of the previous embodiment. The internally cylindrical configuration of the tubular post 28 is shown better in FIG. 7 shown in which, just like in FIG. 6, are the passages indicated with 34 that put the chamber 50 in communication with the atmosphere.

Obviously, the construction details and the embodiments may widely vary with respect to the description and illustration provided above, without for this reason departing from the scope of the invention as defined in the claims.

What is claimed is:

1. Valve connector for medical lines for infusion by means of a fluid introducer, comprising:
    a tubular body having an inlet end designed for the engagement of the introducer, and an outlet end,
    a hollow spike arranged axially into the cavity of the tubular body and having a closed tip facing said inlet end of the tubular body and axially spaced from the latter, said hollow spike being in communication with said outlet end and having a lateral hole spaced from said closed tip for communication with the cavity of said tubular body, and
    a sealing member including:
    an elastic head having a pre-slit and normally arranged in a closure condition in said inlet end of the tubular body, wherein said pre-slit is closed, said elastic head being axially moveable against said closed tip of the hollow spike, upon insertion of said introducer into said inlet end, for interacting with said closed tip taking an elastically deformed condition of opening of said pre-slit,
    an elastic hollow element joined to said head, interposed between said tubular body and said hollow spike and having sealing means in contact with said hollow spike for isolating said lateral hole with respect to the cavity of the tubular body when said head is arranged in the abovementioned undeformed closure condition, said elastic hollow element including an elastic thrust means tending to maintain said head in said closure condition and comprising a base part of said sealing member, having a generally cylindrical axial wall radially spaced from said hollow spike so as to define with the latter an annular chamber; said base part being joined to said elastic hollow element through a generally transverse annular wall which, during the axial movement of said elastic head from said closure condition towards said opening condition, bends inside said annular chamber, and said sealing means of the elastic hollow element including an inner annular projection thereof interacting with an external annular projection of said hollow spike in the opening condition of the elastic head, and further including a substantially inextensible annular member surrounding said elastic hollow element and guided in an axially sliding manner inside said tubular body upon displacement of said elastic head between said closure and opening conditions, in said opening condition said annular member being arranged at an axial position substantially corresponding to said external annular projection.

2. Valve connector according to claim 1, wherein said annular member rigid.

3. Valve connector according to claim 1, wherein said annular chamber communicates with the external of the connector.

4. Valve connector according to claim 1, wherein said base part of the elastic thrust means of said sealing member is blocked axially between said tubular body and a base part of said hollow spike.

5. Valve connector according to claim 1, wherein said elastic head of the sealing member is arranged, in said closure condition, substantially without radial interference in said inlet end of the tubular body.

6. Valve connector according to claim 5, wherein said inlet end of the tubular body has an internal wall formed with axial channels.

7. Valve connector according to claim 1, wherein said closed tip of said hollow spike is configured in such a manner to cause said elastic head of the sealing member to take said opening condition without traversal of said pre-slit.

8. Valve connector according to claim 7, wherein said elastic head has an end wall having an internal annular recess connected to the internal wall of the sealing member through a generally cylindrical part followed by a first portion having a conical surface with lower conicity and by a second portion having a conical surface with greater conicity.

9. Valve connector according to claim 1, wherein said annular member is surrounding the elastic hollow element at an axial position substantially corresponding to said inner annular projection.

10. Valve connector according to claim 9, wherein said means for sealing said elastic hollow element of the sealing member comprise a first and a second internal annular projection axially spaced from each other, arranged on opposite parts with respect to said lateral hole of the hollow spike in the abovementioned closure condition of said elastic head, and of which the first is adapted to interact with said external annular projection of the hollow spike in said opening condition of the elastic head.

11. Valve connector according to claim 10, wherein said first annular projection is maintained, in said closure condition of the elastic head, in sealing contact against a conical surface formed in proximity of said closed tip of said hollow spike.

12. Valve connector according to claim 10, wherein said first annular projection is maintained, in said closure condition of the elastic head, in sealing contact against a cylindrical surface arranged in proximity of said closed tip of said hollow spike.

13. Valve connector according to claim 11, wherein said second internal annular projection is arranged in sealing sliding contact against a portion having a conical surface of said hollow spike which internally delimits said annular chamber and it is divergent towards said outlet end (10) of the connector.

* * * * *